(12) United States Patent
Yamasaki et al.

(10) Patent No.: US 6,242,114 B1
(45) Date of Patent: *Jun. 5, 2001

(54) SOLID FLUORESCENCE REFERENCE AND METHOD

(75) Inventors: Nancy L. S. Yamasaki; Glenn K. Yamamoto, both of Santa Rosa; Lindsey Brown, Healdsburg; Michael W. Shinkle; Blain J. Hendrix, both of Santa Rosa, all of CA (US)

(73) Assignee: Optical Coating Laboratory, Santa Rosa, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/270,933

(22) Filed: Jul. 5, 1994

(51) Int. Cl.$^7$ .............................. B32B 7/00; G01N 21/64; B05D 5/06
(52) U.S. Cl. .............................. 428/690; 428/68; 428/76; 428/173; 428/201; 428/913; 250/461.2; 250/484.4; 250/486.1; 250/487.1; 427/157; 427/419.1
(58) Field of Search .................................. 428/690, 917, 428/913, 691, 411.1, 195, 201, 68, 76, 172, 173; 250/483, 461.2, 483.1, 484.4, 484.5, 486.1, 487.1, 488.1; 427/157, 160, 164, 403, 419.1, 419.2

(56) References Cited

U.S. PATENT DOCUMENTS

| | | | |
|---|---|---|---|
| 4,039,838 | * 8/1977 | DiPiazza | ............................ 250/483 |
| 4,661,704 | * 4/1987 | de Leeun et al. | . |
| 4,865,944 | 9/1989 | Roberts et al. | ....................... 430/495 |
| 4,921,727 | 5/1990 | Datta et al. | ............................ 427/57 |
| 4,975,619 | 12/1990 | Datta et al. | .......................... 313/466 |
| 5,021,327 | 6/1991 | Bunch et al. | ......................... 430/496 |
| 5,039,490 | * 8/1991 | Marsoner et al. | . |
| 5,422,489 | * 6/1995 | Bhargava | . |
| 5,670,375 | * 9/1997 | Seaton et al. | ........................... 436/48 |

FOREIGN PATENT DOCUMENTS 1751825 7/1992 (SU) .

* cited by examiner

Primary Examiner—Marie Yaminitzky
(74) Attorney, Agent, or Firm—Workman, Nydegger & Seeley (57) ABSTRACT

An optical fluorescent composite which controls fluorescence intensity comprises a solid layer containing fluorescent material (such as a phosphor) formed on an optically transparent base or substrate and optically coupled to a spectrally selective filter, also formed on the base or substrate, that modifies the intensity of either or both the excitation or emission spectra of the phosphor. Devices constructed in this manner serve as stable references for fluorescent measurements. Sets of such device is made with filters having different transmittance amplitudes, can characterize fluorescent measurement response over several orders of magnitude. In one of numerous alternative structure, the fluorescent layer can be formed on one substrate, the filter formed on a second substrate and the two substrates joined together.

37 Claims, 6 Drawing Sheets

SOLID FLUORESCENCE REFERENCE AND METHOD

1. BACKGROUND OF THE INVENTION a. Field of the Invention

The present invention relates to so-called fluorescence references which are useful for checking the operation of fluorescence measuring apparatus used in applications such as medical diagnostic technology.

b. Description of the Related Art

Fluorescent materials are used as detection media in areas such as analytical, medical and biological testing or characterization. In fluorescence, a material absorbs light energy and subsequently loses some of that energy by emitting light at a characteristic, and often different, wavelength. In general, detection techniques are structured around a specific reaction or interaction that changes the intensity of a fluorescent signal in relation to the presence of a material of interest.

Figure 1:
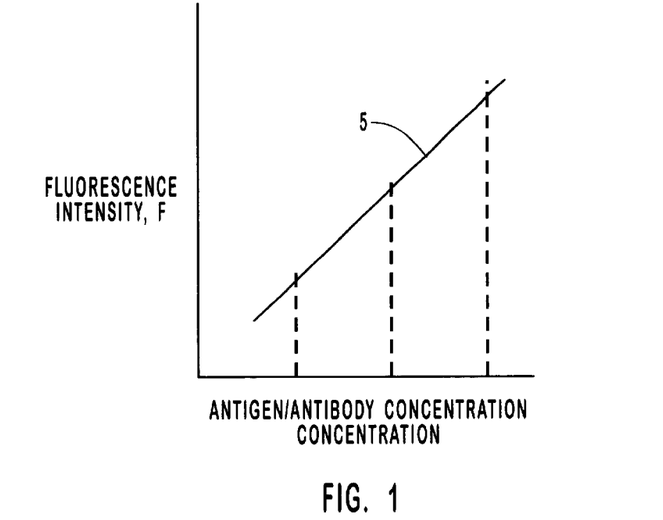
FIG. 1 is a graph of fluorescence intensity as a function of antigen/antibody concentration.

One exemplary application of fluorescence is a test procedure for approximating the concentration of a given antibody in a patient's body fluid using fluorescent-tagged antigens which are specific to the antibody. A sample is prepared which contains the patient's body fluid and fluorescent-tagged antigens. When light of a suitable wavelength is applied to the sample, the fluorescent material will absorb this light and emit characteristic fluorescence at longer wavelengths. If antibodies are present, they will bind with the tagged antigens. The interaction is designed to change the fluorescent signal proportionally and, depending on the type of interaction, the change will be either an increase or a decrease in signal. Therefore, observing the change in the fluorescence gives a direct correspondence to the concentration of the antibodies in the fluid. Signal intensity graph 5 of FIG. 1 illustrates the situation when the signal is increased.

As is well known, fluorescence references are used to check the accuracy of fluorescence-measuring apparatus or instruments.

Common references for fluorescence measurements are organic dyes, which are dissolved to specific concentrations in solvents. The organic dye solution is contained, for example, in cuvettes or dripped into the wells of a test card. The available solvent-dispersed organic dye references do not maintain stable fluorescence values over time and, being liquid, are relatively difficult to shape, handle and store.

As described in the following patents, non-liquid fluorescent materials have been used in control applications. For example, SU patent 1,751,825 describes the combination of a luminophor layer with aluminum and metal oxide absorption layers used in the production of cathode ray tubes. The absorption layer is used to control gas transfer rather than correct light amplitude. Two patents, U.S. Pat. No. 5,021,327 and U.S. Pat. No. 4,865,944, describe different designs incorporating filters and/or fluorescent layers to improve and control radiographic film exposure. This is a significantly different application from fluorescence referencing, and involves X-ray conversion to visible light rather than UV-visible-IR control. U.S. Pat. Nos. 4,975,619 and 4,921,727 describe coatings and the use of coatings on phosphor particles themselves to control triboelectricity rather than optical properties. In their most relevant aspects, the above patents relate directly to: (a) the production of cathode ray tubes (CRTs) or phosphor screens, rather than fluorescence references; (b) the control of physical properties for easier handling, rather than spectral regulation; and (c) conversion of energy for more efficient and uniform exposure of radiographic silver halide films, rather than referenced sources of fluorescence.

2. SUMMARY OF THE INVENTION

In one aspect, the present invention is embodied in a thin film composite for controlling fluorescence intensity, comprising: an optically clear base or substrate of material such as fused silica, glass or plastic; a layer comprising solid fluorescent material such as an inorganic phosphor, formed on the base by wet chemical transfer, including spinning, dipping, or settling, by plasma spraying, or by other suitable techniques; and a spectrally selective filter formed on the base and optically coupled to the fluorescent material-containing layer for modifying the intensity of either or both the excitation or emission spectra of the fluorescent material.

In another aspect, the filter is designed to attenuate or affect the transmission of light in discrete regions of the UV-visible-IR spectra to regulate the specific absorption and/or emission bands of the fluorescent material.

Preferably, the filter is an environmentally stable, dielectric filter comprising coatings of oxides or nitrides of metals such as silicon, tantalum, titanium, zirconium, etc..

Preferably, a clear polymeric or plastic hardcoat protective layer or coating is formed on or encases the layer of fluorescent material to provide increased environmental durability to high temperature and humidity conditions and durability to cleaning and handling. Also, the device may be covered by a thin pieces of material such as clear plastic, fused silica or glass, to further enhance environmental durability to high temperature and humidity conditions and durability to cleaning and handling. Alternatively, this microsheet cover or "slip" can be bonded over the fluorescent material (with or without the hardcoat) for improved durability.

In yet another aspect, the composite fluorescent device according to the present invention is incorporated in a reference device for fluorescent measurement instruments. In one specific embodiment, discrete filters having the same wavelength characteristics but different transmittance amplitudes in the fluorescence emission region, can be combined with the fluorescent material to form a set of fluorescent references that span several orders of magnitude in detected signal. Alternative to this emission attenuation approach, the filters can be designed to control the excitation amplitude of the fluorescent material, or combined emission and excitation modification filters can be used.

The use of stable solid fluorescent materials such as inorganic phosphors and the use of filters comprising stable materials such as dielectrics eliminate the thermal and time-dependent deterioration associated with organic dyes and metallic neutral density filters. However, in some instances, it may be more important to use the identical dye of the diagnostic test, rather than a more stable, but different, inorganic fluorophore. In such instances, coatings of organic dyes could be formed end protected using techniques similar to those described here. This is an alternative, but more limited, embodiment. In addition, solid materials and references allow easier handling, shaping and storage than liquid references. The use of excitation and/or emission modification provides great flexibility in measurement and instrumental fault detection. The application of such materials to fluorescence reference devices satisfies a long-felt, recognized need in the medical diagnostic and analytical instrument technology.

3. BRIEF DESCRIPTION OF THE DRAWING

The above and other aspects of the invention are described with respect to the accompanying drawing, in which.

4. DETAILED DESCRIPTION OF THE PREFERRED EMBODIMENT(S)

Construction and Operation

As alluded to above, the present invention encompasses a composite for controlling fluorescence intensity, which comprises a film or layer of solid fluorescent material such as an inorganic phosphor; and a spectrally selective thin film filter optically coupled to the fluorescent material-containing layer for modifying the intensity of either or both the excitation or emission spectra of the fluorescent material. By way of illustration, various exemplary structures which utilize this concept are disclosed. It is emphasized that the description of such structures is exemplary of the applications of the present invention, and not limiting.

Please note, for convenient reference we sometimes term the layer containing the fluorescent material "phosphor" with the intent that "phosphor" is shorthand for suitable fluorescent materials in general, i.e., with the intent that in so doing we are not limiting the invention to this exemplary material. This shorthand notation is used typically in describing the structure of various composites, for example, the FIG. 3 structure 13 which comprises hardcoat/ "phosphor"/substrate/filter.

Exemplary Reference Structures

Figure 2:
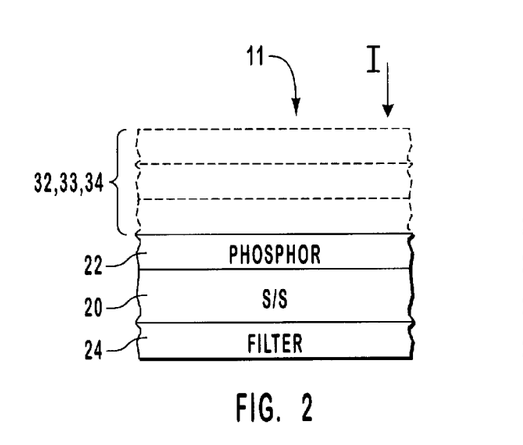
FIGS. 2–10 are simplified cross-section representations of various exemplary, environmentally-protected, controlled fluorescence composites embodying the present invention.
Figure 11:
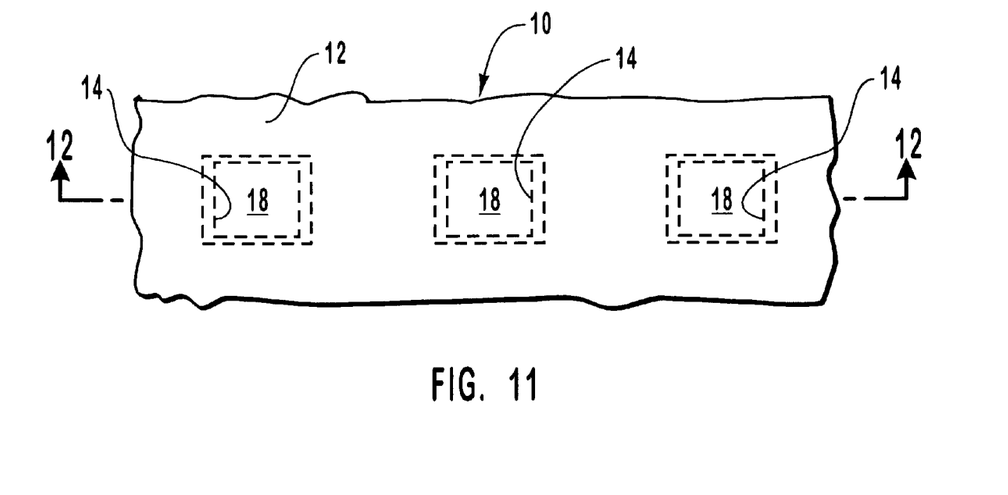
FIG. 11 is a simplified representation of a top plan view of a fluorescence standard card embodying the present invention.
Figure 12:
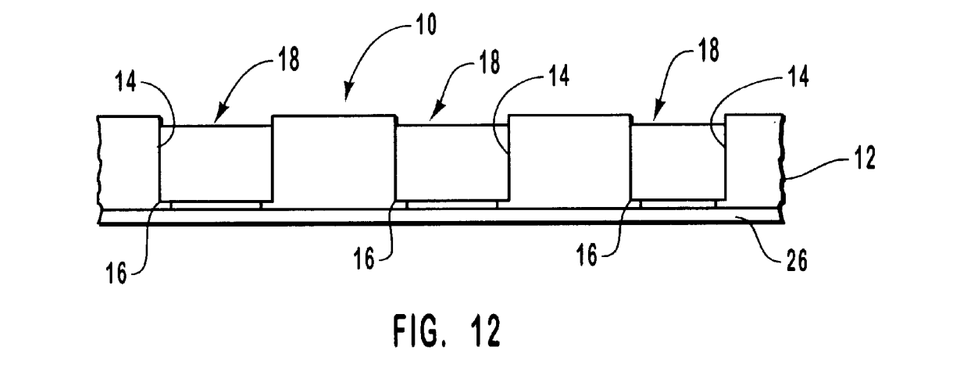
FIG. 12 is an vertical cross-section, not to scale, taken along line 12—12 in FIG. 11.
Figure 13:
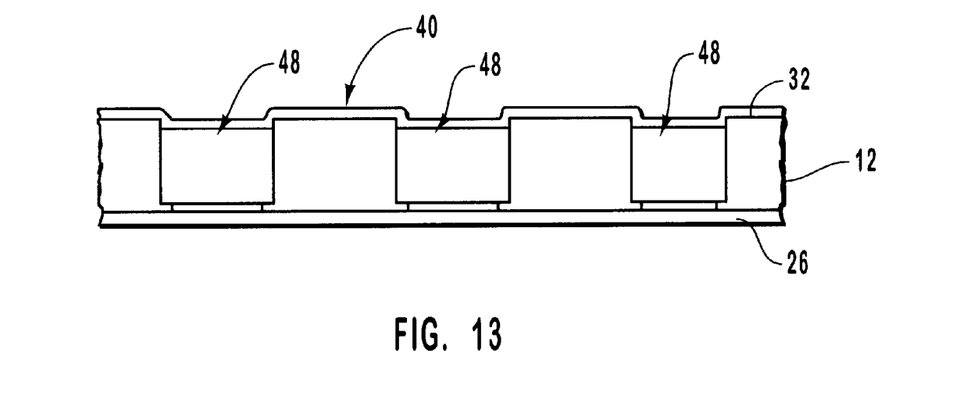
FIG. 13 is a vertical cross-section of an alternative embodiment of the composite of FIGS. 11 and 12.

FIG. 2 depicts a cross-section of an environmentally-protected, controlled fluorescence composite structure 11 which embodies basic principles of the present invention, and which is generic to the controlled fluorescence structures, for example, the card structures depicted in FIGS. 11–13, as well as to other structures and applications. The FIG. 2 composite 11 comprises a substrate 20, a solid layer 22 containing solid fluorescent material such as an inorganic phosphor formed on one side (on one major surface) of the substrate 20 and an optical filter layer 24 formed on the opposite side of the substrate, in the sequence, along the exemplary direction, I, of incident light, phosphor/substrate/ filter. Please note, the structure is referenced to an exemplary direction of incident light for ease of reference, and not by way of limitation. Depending on the system design (e.g., detector location and filter spectral control properties), the incident light, I, may be directed at either the phosphor or the filter surface.

Figure 14:
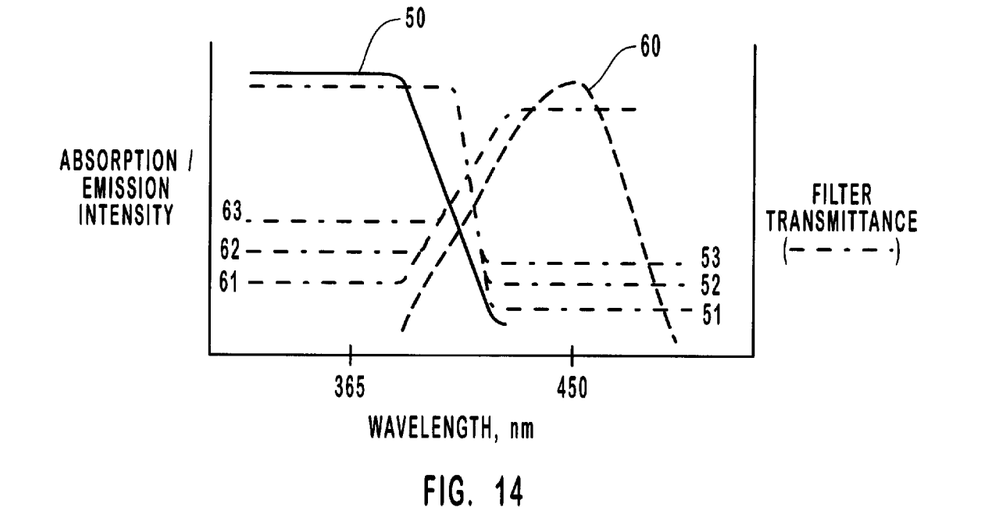
FIG. 14 is a graph of the absorption and emission spectra (absorption and emission intensity as a function of wavelength) for a reference material and relative transmittance for representative filters of the type used in the fluorescence standard card of FIGS. 11–13.

An exemplary inorganic phosphor material, not exhaustive, is Sylvania Type 2461, available from OSRAM Sylvania, Inc. Curves 50 and 60, FIG. 14, are plots of representative absorption and emission spectra (absorption and emission intensity as a function of wavelength) for such phosphor reference materials. These curves and their use are discussed in greater detail relative to the reference cards depicted in FIGS. 11–13. The fluorescent material-containing layer 22 can be formed on the substrate or other supporting surface by wet chemical transfer, including spinning, dipping, or settling, by plasma spraying, or by other suitable techniques.

Preferably, the filter 24 is a spectrally selective, environmentally stable, thin film dielectric filter comprising oxide or nitride coatings, is formed on the substrate or other support by standard techniques such as high vacuum evaporation, sputtering, ion beam or chemical vapor deposition, and is optically coupled to the fluorescent material-containing layer 22, for modifying the intensity of either or both the excitation or emission spectra of the fluorescent material.

In another aspect, the filter 24 is designed to affect the transmission of light in discrete regions of the UV-visible-IR spectra to regulate the specific absorption and/or emission bands of the fluorescent material. The filters can be designed to modify only emission or excitation amplitude of the fluorescent material, or combined emission and excitation modification filters can be used.

One or more protective layers can be formed over at least the fluorescent layer 22, for example, to provide increased environmental durability to temperature and humidity, and increased durability to handling and cleaning. The protective layers include an optional but preferred protective hardcoat layer 32 of material such as hard, optically clear polymer or plastic, formed over the fluorescent layer 22. Preferably the hardcoat 32 is a material such as hard, optically transparent polysiloxane (for example, Exxene S-28-1), which can be formed over the layer 22 by a number of suitable techniques, including spray or flow coating, etc. An encapsulation layer 33 of material such as epoxy can be formed on the composite, typically over the fluorescent layer 22. In another alternative, a hard durable slip or cover 34 of material such as glass, fused silica, hard plastic, etc., can be formed over the composite alone, or in combination with the encapsulation material, to provide even greater durability in elevated temperature and humidity environments and to handling and cleaning. Examples of the cover/slip materials include MICROSHEET™ (a very thin glass) available from Corning, Inc. fused silica and BK-7 Schott glass.

In general, possible individual and combination protective structures include hardcoat 32; encapsulation 33; hardcoat 32 and encapsulation 33; slip 34; hardcoat 32 and slip 34; encapsulation 33 and slip 34; and hardcoat 32, encapsulation 33 and slip 34. As indicated by the dotted lines representing layers 32, 33 and 34, FIG. 2 is intended to represent all the various possibilities and combinations of one, two or three protective layers, as well as any additional layers such as the adhesive 35 (see below) for joining the layers. The adhesive material can serve both protection and joining functions. An example of such a suitable adhesive is Tra-Bond F-113, available from Tra-Con, Inc. of 55 North Street, Medford, Me., 02155. In fact, we have used this same material as an adhesive layer 35 and as an encapsulation layer 33, thereby providing substantially similar protective functions in both applications. It should be noted that the substrate(s), adhesive(s), etc. preferably are optically transparent over the wavelength range of interest.

Figure 5:
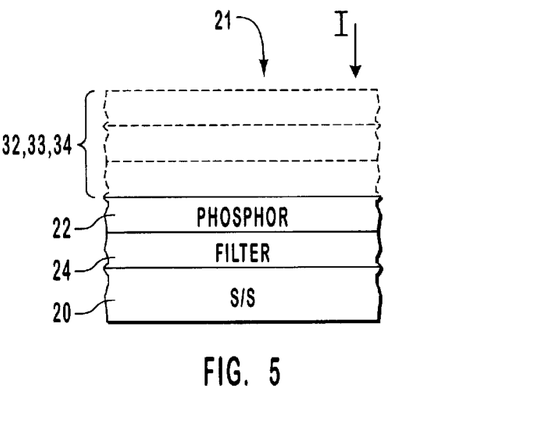

FIG. 5 depicts a protected, controlled fluorescence composite 21 which differs from the protected, controlled fluorescence composite 11, FIG. 2, in that the filter layer 24 and the fluorescent material-containing layer 22 are formed on the same side of the substrate, preferably with the filter 24 between the substrate and the fluorescent layer. This arrangement 21 of phosphor/filter/substrate has the advantage of affording even greater protection potentially against environment, handling, cleaning, etc., in that both the filter 24 and the fluorescent layer 22 are covered and protected on both sides.

Figure 3:
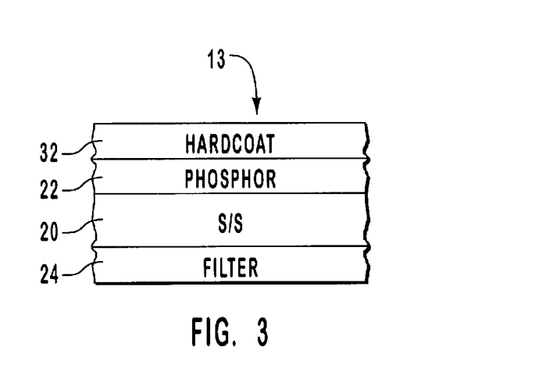
Figure 4:
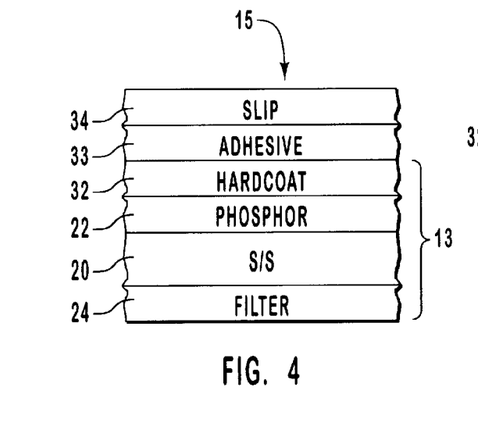

FIGS. 3 and 4 depict individual protected, controlled fluorescence embodiments 13 and 15 selected from the range depicted by FIG. 2. The controlled fluorescence composite 13 of FIG. 3 comprises the FIG. 2 combination of a substrate 20 having a solid layer 22 containing fluorescent material and an optical filter layer 24 formed on opposite sides of the substrate, and in addition has a protective hardcoat 32 formed on the fluorescent layer 22, resulting in the structure hardcoat/phosphor/substrate/filter.

The controlled fluorescence composite 15 of FIG. 4 comprises the composite 13 of FIG. 3 and, in addition, comprises a cover or slip 34 of glass, fused silica, hard plastic, etc. formed on the protective hardcoat 32 to provide even greater durability in elevated temperature and humidity environments and to handling and cleaning. As shown, the slip 34 can be adhered to the protective hardcoat coating 32 by adhesive 33, such as the previously mentioned Tra-Bond F-113.

Figure 6:
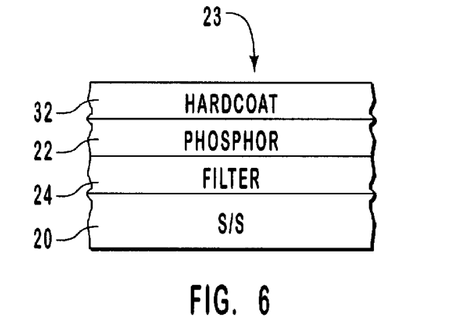
Figure 7:
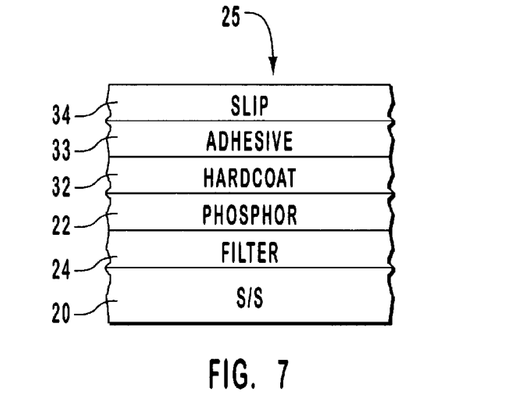

FIGS. 6 and 7 depict individual protected, controlled fluorescence embodiments 23 and 25 selected from the range depicted in FIG. 5. The controlled fluorescence composite 23 of FIG. 6 comprises the FIG. 5 combination in which a fluorescent material-containing layer 22 and a filter 24 are formed on the same side of the substrate 20 and the fluorescent layer is formed over the filter. Composite 23 further comprises protective hardcoat 32, giving the following structure: hardcoat/phosphor/filter/substrate.

The FIG. 7 structure 25 comprises the controlled fluorescence structure 23 of FIG. 6 with the addition of the adhesively bonded slip 34, providing the following structure: slip/adhesive/hardcoat/phosphor/filter/substrate. As alluded to previously, in structures 23 and 25, the filter 24 and the fluorescent layer 22 are protected on one side by the substrate 20 and on the opposite side by the protective layer 32 (23, FIG. 6) or by the protective layers 32, 33 and 34 (25, FIG. 7), which affords even greater protection than the single protective layer.

Figure 8:
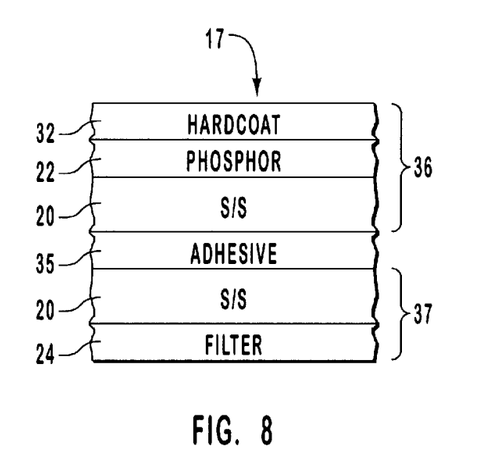

Referring to FIG. 8, in another exemplary embodiment 17, and to facilitate manufacture and/or protect the filter and the fluorescent material, the fluorescent layer 22 can be formed on one substrate 20, the filter 24 formed on a second substrate 20 and the two substrates then joined back to back, as by an adhesive layer 35. The protective layer(s) such as hardcoat 32 can be formed before the substrates are joined, e.g., as part of the fabrication of the two substrate composite subassemblies 36 and 37, or after the substrate composites are joined. The sequence of the structure 17, FIG. 8, which is made in accordance with this alternative design is: hardcoat/phosphor/substrate #1/laminate (adhesive)/substrate #2/filter. Where the protective layer(s) such as hardcoat 32 encapsulates the composite (that is, is formed on both major surfaces of the composite, here on the fluorescent layer 22 and the filter), the protective layer(s) preferably is (are) formed after the composite subassemblies.

Figure 9:
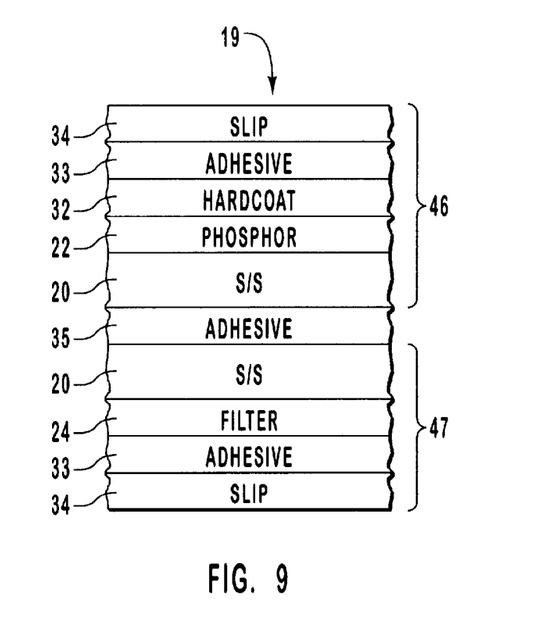

FIG. 9 depicts structure 19, which adds to composite 17 the optional cover or slip 34. Typically the slip 34 covers both substrates and thus preferably is formed after the substrate composite subassemblies composites 46 and 47 are joined. The laminate or adhesive layers 35 joining the substrates and the adhesive layer 33 joining the slip 34 to the composite can be epoxy material of the type described above. Please note, typically the words/terms "slip" and "cover" have the connotation of a discrete solid piece of material which covers or is applied to a construct, whereas "hard coat," "adhesive" and "encapsulation" imply layers that originally flow and then take on a more solid form. More generally, in this context, these terms have in common the connotation of environmentally protective cover means.

Figure 10:
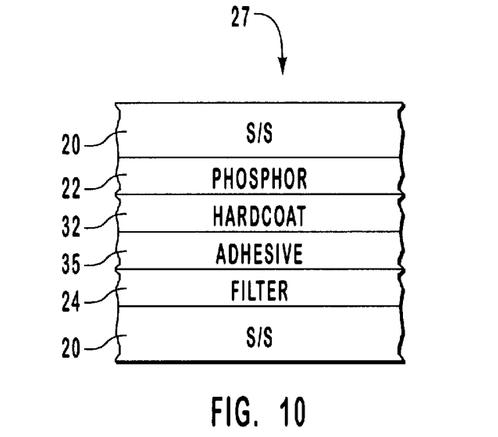

FIG. 10 depicts yet another of the possible two-substrate embodiments, an embodiment 27 in which the two substrates provide outer protection and the fluorescent layer may be protected internally by an optional hardcoat layer 32. The overall structure is: substrate#1/phosphor/optional hardcoat/adhesive/filter/substrate #2.

Exemplary Reference Cards

FIGS. 11 and 12 are, respectively, a simplified top plan view and a longitudinal vertical section view, expanded vertically for ease of understanding, of an exemplary solid fluorescence material, emission-attenuated reference card 10 in accordance with the present invention. The basic card itself is well known in the relevant technology, and comprises preferably a support or base or substrate 12, of material such as glass or plastic, having so-called "wells" (optically transparent regions or physical holes) 14 extending from one major surface to the other, illustratively from the top to the bottom surface. (As used here, "optically transparent" or "optically clear" refers to material which is transmissive to radiation over the wavelength range of interest.) Referring to FIG. 12, the base 12 itself may be mounted on a second base or substrate 26, such as a microscope slide. A lip or ledge 16 which circumscribes the bottom of each well or plastic laminate 14 provides support for discrete bodies 18. The bodies 18 have, for example, the structure of composite 15, FIG. 4, that is, slip/adhesive/hardcoat/phosphor/substrate/filter. As alluded to above, curves 50 and 60, FIG. 14, are plots of representative absorption and emission spectra (absorption and emission intensity as a function of wavelength) for the exemplary Sylvania 2461 phosphor reference materials used, in the reference card 10.

FIG. 13 depicts an alternative embodiment 40 of the card structure 10 of FIGS. 11 and 12 which is similar to embodiment 10, but uses protected, fluorescence bodies 48 which have the structure 13, FIG. 3, comprising hardcoat/phosphor/substrate/filter. In addition, this alternative card structure is encapsulated or laminated with a protective hardcoat coating 32 of material such as the aforementioned Exxene S-28-1. The protective hardcoat encapsulation coating 32 typically is formed over at least the upper surface of the device 40, by dip, spray, flames coating, or other suitable techniques, after the reference samples 48 are mounted in the wells 14. The encapsulation form of the hardcoat 32 used here seals the edges between the samples 48 and the substrate 12.

In one presently preferred embodiment, the three illustrated reference samples 18 (or the three illustrated reference samples 48) are identical (the concentration of fluorescent material is identical), except for the filters, which are designed to control the emission of the fluorescence material in the associated wells. In exemplary embodiments of the FIGS. 12 (or 13) design, the three filters 24 are conventionally constructed short ware pass filters designed to transmit for example 0.04%, 0.4% and 4% of the emitted radiation at the peak of the emission spectra associated with the fluorescence material.

The operation of the short wave pass, 0.04%, 0.4% and 4% filters is depicted by FIG. 14 curves 51, 52, 53, respectively. Plots of the three (or more) points of emitted radiation intensity at a given wavelength typically approximate a straight line, similar to that of graph 5, FIG. 1. This plot can be compared to data generated by the instrument in question, in a manner well known in the technology, to verify that operation of the instrument is within specifications. For example, from past use/testing, it is known that given concentrations of the fluorophore used in an antibody/antigen test will provide a given transmittance or emission plot when the apparatus is operating properly. A reference card containing material having similar transmittance or emission response, but composed of the stable phosphor and the 0.04%, 0.4% and 4% filters then can be used to verify that the machine operation is to specification.

Alternatively, identical filters 24, FIGS. 2–10, can be used in combination with different concentrations of fluorescent material in the layers 22 of the different reference samples 18 in FIG. 12 (or samples 48 of FIG. 13), designed to give the desired different fluorescent intensity for each sample.

Discrete reference samples (18 of FIGS. 11 and 12) are conveniently made by forming the fluorescent and thin film filter layers 22 and 24 on opposite sides of a sheet or panel of the substrate material 20, then cutting the coated substrates to form the discrete samples 18. The protective hardcoat coating 32 can be formed before or after the cutting step. Alternately, the phosphor/filter combinations of FIGS. 4–10 can be constructed for increased durability and ease of handling, and cut to size for wells 14. The result is discrete, essentially complete reference samples which are inserted into the wells 14. To enhance the protection provided by the protective coating 32 or slip 34, the reference samples can be sealed to the surrounding substrate 12 by bonding epoxy around their edges. The process of forming discrete reference samples 48 of FIG. 13 is the same as the process for samples 18 of FIG. 12, except that the hardcoat 32 is an encapsulation and thus is formed after the discrete devices 48 are mounted in wells 14.

Other Reference Configurations

Figure 15:
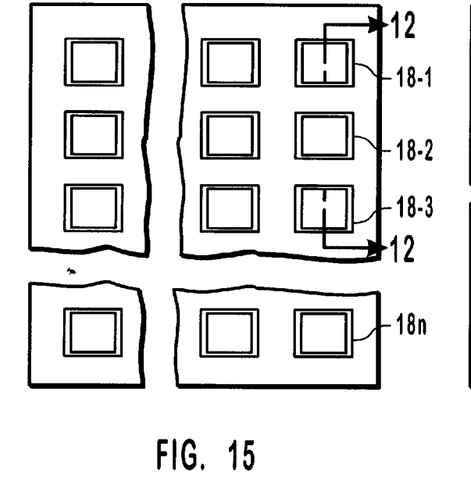
FIGS. 15 and 16 are simplified representations of plan views of exemplary reference cards.
Figure 16:
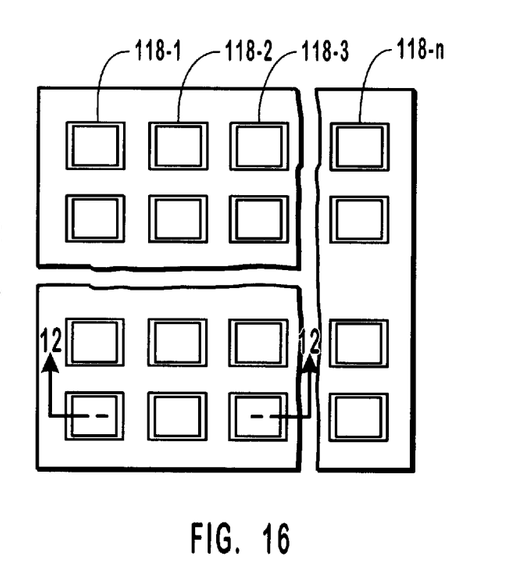

Please note, the three-well reference card 10 is only one of many possible reference configurations. For example, one standard fluorescence test card (of the type which is used for testing for antibodies, toxins, etc.) contains a large number of wells arranged in rows and columns. FIGS. 15 and 16 depict examples of such multi-well diagnostic systems.

Using the sample 18 as an example, a number of individual samples 18-1, 18-2, . . . 18-n, or portions of or entire rows or columns of wells 118-1, 118-2, . . . 118-n, could be dedicated to the above-discussed references, thus providing a card that is a combination reference/test card. (The three-well reference of FIGS. 11 and 12 is given by way of convenient illustration only; obviously, as indicated in FIGS. 15 and 16, fewer or more references can be used.)

Figure 17:
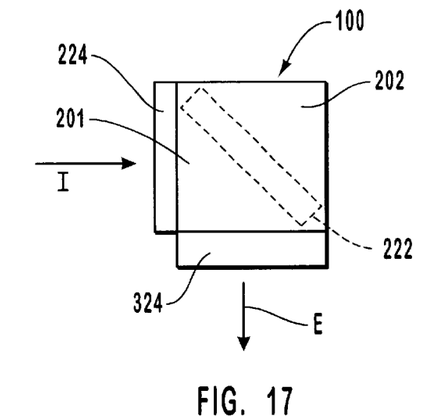
FIG. 17 depicts a 90° detection system comprising a phosphor layer and a filter layer bonded to prisms mounted within a cuvette holder.
Figure 18:
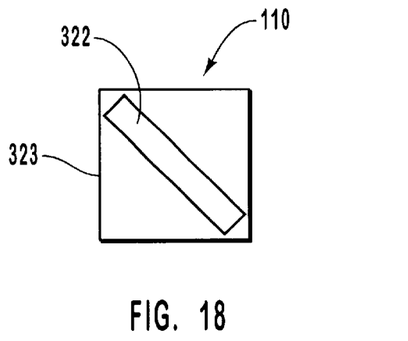
FIGS. 18 and 19 are top and perspective views of a detection system in which the fluorescent phosphor/filter combination is in the form of a discrete slab which is mounted in a standard cuvette holder.
Figure 19:
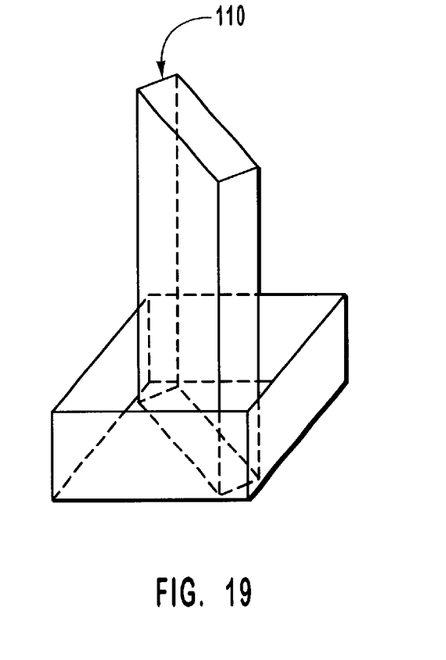
Figure 20:
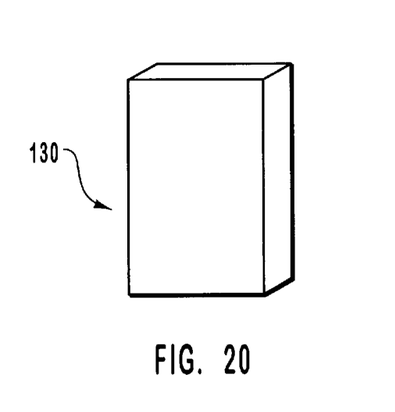
FIGS. 20 and 21 depict rectangular and circular single sample systems.
Figure 21:
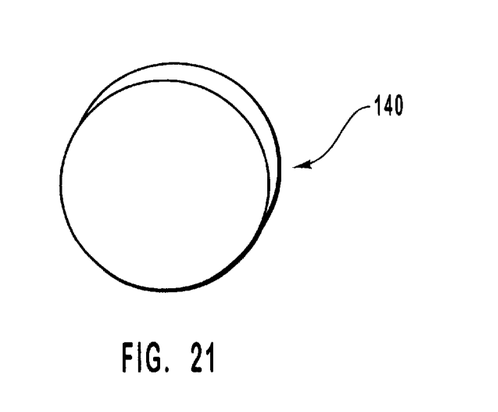

Other exemplary configurations are shown in FIGS. 17–21. FIG. 17 shows a 90° detection system 100 in which the fluorescent phosphor layer 222 is bonded between the prisms 201 and 202 sized to fit a standard cuvette holder, and a thin film excitation filter 224 and/or a thin film emission filter 324 are bonded to or deposited onto the outer sides of the prisms. Incident and emitted radiation paths are denoted I and E, respectively. FIGS. 18 and 19 are top and perspective views of a detection system 110 in which the solid fluorescent phosphor/filter combination is in the form of a discrete slab 322, which is mounted in a standard cuvette holder 323. Finally, FIGS. 20 and 21 illustrate rectangular and circular single sample systems 130 and 140. FIGS. 18–21 are discrete samples based on constructions such as those described in FIGS. 2–10.

Alternative Filters, Including Emission/Absorption Modification

The above-mentioned emission attenuation is presently preferred because it ensures that the constant irradiance which is used with the test samples is maintained during the instrument check, eliminating one potential variable. In addition, it avoids the potential problem of cutting down the excitation light such that a non-linear excitation/emission relationship results. However, with a good understanding of the fluorescent systems to be used, absorption modification is an alternative approach. For example, long wave pass filters 24 having spectral characteristics such as are depicted at 61, 62, 63, FIG. 14, can be used to control the percentages of incident light in the absorption spectrum which reach the given fluorescent material. This excitation modification controls the emitted light in a manner complementary or analogous to the previous embodiment for controlling emission.

In another embodiment, both absorption and emission can be modified, for example, by using filters 24 which comprise stacks of short wave pass and long wave pass filters.

In addition to short wave pass and/or long wave pass filters, neutral density or absorbing filters can be used for both absorption/excitation modification and emission attenuation. The use of oxide or nitride coatings is preferred to pure metal films for increased durability in this configuration. However, in applications with sufficient environmental protection, neutral density or absorbing filters containing metals or dyes may be useable. Although several different glass absorption type filters are available from various manufacturers, the variety is not large. In contrast, the spectral behavior of interference filters is completely adjustable through the thin film thicknesses.

EXAMPLES

Dielectric filters controlling light in the UV, visible, and/or IR region were formed by standard vacuum coating techniques. The filters were designed to pass maximum light intensity in the excitation band of a phosphor material, but to transmit only a controlled amount of the emitted (fluorescent) light. Specifically, for $Eu^{+2}$-doped phosphor, the filter was designed for maximum transmittance at 365 nm, but only limited transmittance at 450 nm, near the fluorescence maximum. Separate filters were then designed to transmit discrete amounts of the fluorescence intensity, such as 10%, 5%, 1%, 0.3%, etc. Filters and phosphor were applied to a range of transmitting base or substrates including common glass, colored glass, fused silica, etc.

In specific examples, discrete reference devices 18 having the structure 15, FIG. 4, were formed having the following construction/characteristics:

slip/adhesive/hardcoat/phosphor/substrate/filter #1;
slip/adhesive/hardcoat/phosphor/substrate/filter #2;
slip/adhesive/hardcoat/phosphor/substrate/filter #3;

where filters #1, #2, #3, transmitted, respectively, 0.04%, 0.4% and 4% of the characteristic light emitted from the phosphor used. (For convenience, these three designs are designated "low," "medium," and "high.") $Eu^{+2}$-doped Sylvania Type 2461 phosphor was suspended in a barium acetate/potassium silicate aqueous solution and applied by liquid settling techniques to achieve a surface density of about 3.5 $mg/cm^2$ directly onto glass samples 20. (This is a standard process well known to those in the phosphor industry, and was supplied by Sylvania.) The glass had been coated previously on the opposite side with an optical thin film, short wave pass #1, #2 or #3 filter. A protective plastic "hard" coating 32 of Exxene S-28-1 material was formed by coating over the deposited phosphor film.

Tra-Bond® F-113 optically clear epoxy was used to bond a slip 34 of Corning 0211 MICROSHEET onto the hard-coated phosphor surface for further protection. This construction passed extended environmental testing (5 days at 50° C. and 95% relative humidity).

Figure 22:
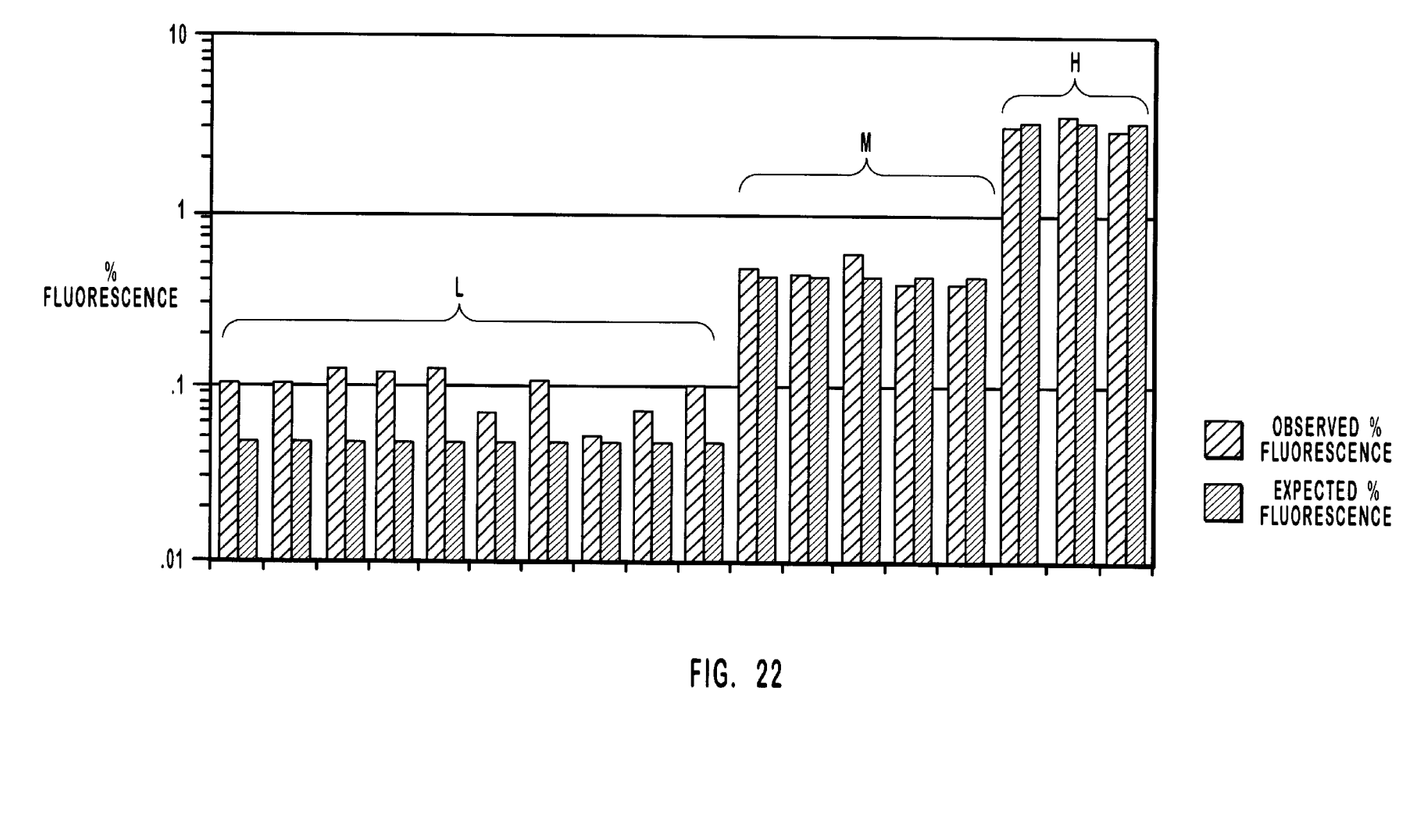
FIG. 22 is a bar chart of fluorescence intensity for multiple test runs of low, medium and high reference samples constructed in accordance with FIG. 4, based upon readings obtained before the samples were placed in an associated card.

The optical performance of these references is shown in FIG. 22, which depicts the fluorescence, expected and observed, for multiple test runs of each of low, medium and high fluorescence reference samples. The groupings of low, medium and high fluorescence reference samples are designated, respectively, L, M and H in the figure. The expected fluorescence intensity was calculated based on the convolution of the filter and phosphor performances at the wavelength of interest (450 nm), and compared to the observed fluorescence at the same wavelength. Approximately one order of magnitude decrease in intensity was expected for each of the three reference designs. The high and medium fluorescence reference designs show good agreement between observed and expected values. The low fluorescence references gave signals near the sensitivity/noise limit of our instrument, and this is likely the cause of the poorer agreement.

One distinct advantage of the present invention is that adjustment of fluorescence levels requires only well-known modifications of production filter coating designs. Thus, virtually any discrete fluorescence level is accessible, and once chosen, can be achieved by a standard, repeatable method.

Having thus described preferred and alternative embodiments of the coating of the present invention, those of usual skill in the art will readily develop additional modifications and embodiments which are within the scope of the invention, limited only by the scope of the appended claims.

What is claimed is:

1. A durable fluorescence reference comprising:
   an optically clear base or substrate;
   a layer containing solid inorganic fluorescent material on a selected region of the base or substrate and having the characteristic of emitting light in a given wavelength band in response to absorption of incident light within a selected wavelength band; and
   an optical filter on the base or substrate and optically coupled to the selected region for modifying at least one of the absorption band of light and the emission band of light.

2. The reference of claim 1, wherein the filter is adapted for modifying the emission band of light.

3. The reference of claim 1, wherein the filter is adapted for modifying the absorption band of light.

4. The reference of claim 1, wherein the reference structure is inorganic fluorescent layer/substrate/filter.

5. The reference of claim 1, wherein the reference structure is inorganic fluorescent layer/filter/substrate.

6. The reference of claim 1, wherein the reference structure is selected from (A) inorganic fluorescent layer/first substrate/joining means/second substrate/filter and (B) inorganic fluorescent layer/first substrate/joining means/filter/second substrate.

7. The reference of claim 1, further comprising a protective hardcoat over at least the inorganic fluorescent layer for increasing durability.

8. The reference of claim 7, further comprising a protective slip covering the reference, for increasing durability and facilitating handling, the protective slip comprised of glass or fused silica.

9. The reference of claim 1, further comprising a protective slip covering the reference, for increasing durability and facilitating handling, the protective slip comprised of glass or fused silica.

10. The reference of claim 1, wherein the reference structure comprises hardcoat/inorganic fluorescent layer/substrate/filter.

11. The reference of claim 1, wherein the reference structure comprises hardcoat/inorganic fluorescent layer/filter/substrate.

12. A durable fluorescence reference comprising:
   first and second optically clear bases or substrates, each having first and second opposite major surfaces;
   a solid layer containing inorganic fluorescent material on the first surface of the first base or substrate and having the characteristic of emitting light in a selected wavelength band in response to absorption of incident light within a selected wavelength band;
   an optical filter on the first surface of the second base or substrate, the first and second bases or substrates being joined along their second surfaces, such that the optical filter is optically coupled with the layer containing inorganic fluorescent material for modifying at least one of the absorption band of light and the emission band of light; and
   a protective slip on the reference and comprised of glass or fused silica.

13. A process for forming a composite for a fluorescence reference, comprising:
   providing an optically clear base or substrate;
   forming a thin film dielectric filter on the base or substrate, the filter comprising materials selected from oxide- and nitride-containing materials; and
   forming a solid layer containing inorganic fluorescent material on the base or substrate and having the characteristic of emitting light in a selected wavelength band in response to absorption of incident light within a selected wavelength band, said filter being adapted for modifying at least one of the absorption and emission spectra of the fluorescent material.

14. The process of claim 13, wherein the solid layer of fluorescent material is formed by wet chemical transfer.

15. The process of claim 13, further comprising forming a protective hardcoat coating over the layer containing the fluorescent material.

16. The process of claim 13, further comprising encapsulating the composite in an optically clear protective coating.

17. The process of claim 15, further comprising forming or applying an optically clear cover slip over the composite.

18. The process of claim 15, further comprising encapsulating the composite in an optically clear protective cover and forming or applying an optically clear cover slip over the composite.

19. The process of claim 13, further comprising forming a protective hardcoat coating over the layer containing the fluorescent material; cutting the composite into discrete reference samples; and mounting the reference samples in a reference card.

20. The process of claim 19, further comprising encapsulating the reference card in an optically clear protective cover.

21. The process of claim 19, further comprising forming or applying an optically clear cover slip over the reference card.

22. The process of claim 19, further comprising encapsulating the reference card in an optically clear protective cover and forming an optically clear cover slip over the reference card.

23. The process of claim 13, further comprising forming a protective hardcoat coating over the layer containing the fluorescent material; adhering a cover slip over the composite; cutting the composite into discrete reference samples; and mounting the reference samples in a reference card.

24. The process of claim 23, further comprising encapsulating the reference card in an optically clear protective cover.

25. The process of claim 23, further comprising forming or applying an optically clear cover slip over the reference card.

26. The process of claim 23, further comprising encapsulating the reference card in an optically clear protective cover and forming an optically clear cover slip over the reference card.

27. A fluorescence reference card, comprising:
   a substrate having a plurality of wells formed therein;
   a plurality of fluorescent samples mounted within the wells, the samples comprising:
      an optically clear base;
      a layer containing solid inorganic fluorescent material on a selected region of the base and having the characteristic of emitting light in a given wavelength band in response to absorption of incident light within a selected wavelength band;
      an optical filter on the base and optically coupled to the selected region for modifying at least one of the absorption band of light and the emission band of light; and
      a protective hardcoat over at least the fluorescent layer for increasing durability.

28. The reference card of claim 27, further comprising a protective slip covering the card, for increasing durability and facilitating handling.

29. A durable fluorescence reference comprising:
   an optically clear base or substrate;
   a plurality of selected regions of the base or substrate having solid inorganic fluorescent material thereon with the characteristic of emitting light in a given wavelength band in response to absorption of incident light within a selected wavelength band; and
   a plurality of optical filters on the base or substrate and optically coupled to the selected regions for modifying at least one of the absorption band of light and the emission band of light.

30. The reference of claim 29, wherein the filters are each adapted for allowing a desired amount of light throughput for at least one of the absorption band of light and the emission band of light.

31. The reference of claim 29, wherein the filters are adapted for modifying the emission band of light.

32. The reference of claim 29, wherein the filters are adapted for modifying the absorption band of light.

33. A durable fluorescence reference comprising:
   an optically clear base or substrate;
   a layer containing solid inorganic fluorescent material on a selected region of the base or substrate and having the characteristic of emitting light in a given wavelength band in response to absorption of incident light within a selected wavelength band;
   an optical filter on the base or substrate and optically coupled to the selected region for modifying at least one of the absorption band of light and the emission band of light;
   a hardcoat on the inorganic fluorescent layer;
   an adhesive layer on the hardcoat; and
   a slip on the adhesive layer;
   wherein the reference structure comprises slip/adhesive layer/hardcoat/inorganic fluorescent layer/ base or substrate/filter.

34. A durable fluorescence reference comprising:
   an optically clear base or substrate;
   a layer containing solid inorganic fluorescent material over a selected region of the base or substrate and having the characteristic of emitting light in a given wavelength band in response to absorption of incident light within a selected wavelength band;
   an optical filter on the base or substrate and optically coupled to the selected region for modifying at least one of the absorption band of light and the emission band of light;
   a hardcoat on the inorganic fluorescent layer;
   an adhesive layer on the hardcoat; and
   a slip on the adhesive layer;
   wherein the reference structure comprises slip/adhesive layer/hardcoat/inorganic fluorescent layer/filter/ base or substrate.

35. A durable fluorescence reference comprising:
   a first optically clear base or substrate;
   a layer containing solid inorganic fluorescent material on a selected region of the first base or substrate and having the characteristic of emitting light in a given wavelength band in response to absorption of incident light within a selected wavelength band;
   a hardcoat on the inorganic fluorescent layer;
   a second optically clear base or substrate;
   an adhesive layer between the first and second bases or substrates; and
   an optical filter on the second base or substrate and optically coupled with the selected region for modifying at least one of the absorption band of light and the emission band of light;
   wherein the reference structure comprises hardcoat/ inorganic fluorescent layer/first base or substrate/ adhesive layer/second base or substrate/filter.

36. A durable fluorescence reference comprising:

a first optically clear base or substrate;

a layer containing solid inorganic fluorescent material on a selected region of the first base or substrate and having the characteristic of emitting light in a given wavelength band in response to absorption of incident light within a selected wavelength band;

a second optically clear base or substrate;

an optical filter on the second base or substrate and optically coupled with the selected region for modifying at least one of the absorption band of light and the emission band of light;

a hardcoat on the inorganic fluorescent layer;

a first adhesive layer on the hardcoat;

a first slip on the first adhesive layer;

a second adhesive layer between the first and second bases or substrates;

a third adhesive layer on the filter; and a second slip on the third adhesive layer;

wherein the reference structure comprises first slip/first adhesive layer/hardcoat/inorganic fluorescent layer/first base or substrate/second adhesive layer/second base or substrate/filter/third adhesive layer/second slip.

37. A durable fluorescence reference comprising:

a first optically clear base or substrate;

a second optically clear base or substrate;

a layer containing solid inorganic fluorescent material on a selected region of the first base or substrate and having the characteristic of emitting light in a given wavelength band in response to absorption of incident light within a selected wavelength band;

an optical filter on the second base or substrate and optically coupled with the selected region for modifying at least one of the absorption band of light and the emission band of light;

a hardcoat on the inorganic fluorescent layer; and an adhesive layer between the hardcoat and the filter;

wherein the reference structure comprises first base or substrate/inorganic fluorescent layer/hardcoat/adhesive layer/filter/second base or substrate.

* * * * *